US012603336B2

(12) United States Patent
Wiebenga et al.

(10) Patent No.:  US 12,603,336 B2
(45) Date of Patent:  Apr. 14, 2026

(54) BATTERY MONITORING SYSTEM FOR MEASURING HYDROGEN CONCENTRATION TO DETECT BATTERY CELL OVERTEMPERATURE AND PREDICT THERMAL RUNAWAY

(71) Applicant: GM GLOBAL TECHNOLOGY OPERATIONS LLC, Detroit, MI (US)

(72) Inventors: Michelle H. Wiebenga, Farmington Hills, MI (US); Rasoul Salehi, Ann Arbor, MI (US); Lei Wang, Rochester Hills, MI (US); Wei Li, Troy, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 624 days.

(21) Appl. No.: 18/073,021

(22) Filed: Dec. 1, 2022

(65) Prior Publication Data

US 2024/0186599 A1     Jun. 6, 2024

(51) Int. Cl.
*H01M 10/48*          (2006.01)
*G01N 33/00*          (2006.01)
(Continued)

(52) U.S. Cl.
CPC .......... *H01M 10/48* (2013.01); *G01N 33/005* (2013.01); *H01M 10/425* (2013.01);
(Continued)

(58) Field of Classification Search
CPC ...... B60L 2240/545; B60L 58/22; B60L 3/12; B60L 58/10; G01N 33/005; G01N 33/0036; G01N 33/0027; G01N 33/0009;

G01R 31/396; G01R 19/16542; G01R 31/382; H01M 10/48; H01M 10/42; H01M 50/317; H01M 50/325; H01M 50/30;
(Continued)

(56) References Cited

U.S. PATENT DOCUMENTS 5,666,040 A * 9/1997 Bourbeau ......... H01M 10/4257
                                                  320/147
2004/0261500 A1* 12/2004 Ng ........................ B82Y 15/00
                                                  73/31.05
(Continued)

FOREIGN PATENT DOCUMENTS

CN        114613932 A       6/2022
KR    20220158204 A * 11/2022 .......... H01M 50/249

OTHER PUBLICATIONS

Essl, Christiane & Seifert, Lauritz & Rabe, Michael & Fuchs, Anton. (2021). Early Detection of Failing Automotive Batteries Using Gas Sensors. Batteries. 7. 25. 10.3390/batteries7020025. (Year: 2021).*
(Continued)

*Primary Examiner* — Catherine T. Rastovski
*Assistant Examiner* — Eric Sebastian Von Wald

(57)          ABSTRACT

A battery monitoring system includes a hydrogen sensing system configured to selectively measure a plurality of hydrogen concentrations in a plurality of battery cells, respectively. A controller is configured to detect battery cell overtemperature in at least one of the plurality of battery cells in response to a corresponding one of the plurality of measured hydrogen concentrations of the plurality of battery cells.

16 Claims, 4 Drawing Sheets

(51) Int. Cl.
*H01M 10/42* (2006.01)
*H01M 10/44* (2006.01)
*H01M 50/317* (2021.01)
*H02J 7/90* (2026.01)

(52) U.S. Cl.
CPC ....... *H01M 10/443* (2013.01); *H01M 50/317* (2021.01); *H02J 7/973* (2026.01)

(58) Field of Classification Search
CPC ............. H01M 10/425; H01M 10/443; H01M 10/441; H01M 10/482; H01M 10/486; H01M 2010/4271; H01M 10/625; H01M 2220/20; H01M 10/63; H01M 10/4228; H01M 10/44; H01M 10/652; H01M 10/6557; H01M 2200/00; H01M 50/284; H01M 50/574; H01M 50/581; H01M 10/4257; H01M 10/4285; H01M 10/46; H10M 10/617; H02J 7/00719; H02J 7/007192; H02J 7/0029; H02J 7/00309; H02J 2310/48; Y02T 10/70; Y02T 10/72; Y02T 90/16
See application file for complete search history.

(56) References Cited

U.S. PATENT DOCUMENTS

| | | | |
|---|---|---|---|
| 2011/0059341 A1 | 3/2011 | Matsumoto et al. | |
| 2011/0199056 A1* | 8/2011 | Pinto, IV ............ | H01M 10/441 |
| | | | 320/152 |
| 2021/0043900 A1* | 2/2021 | Al-Ghanim ............... | F24F 7/00 |
| 2021/0245627 A1 | 8/2021 | Ferguson et al. | |
| 2022/0085428 A1* | 3/2022 | Engle ................... | H01M 10/443 |
| 2022/0402354 A1* | 12/2022 | Wang ................... | H01M 50/249 |
| 2023/0141687 A1* | 5/2023 | Kenney ............. | H01M 10/4242 |
| | | | 429/402 |

OTHER PUBLICATIONS

U.S. Appl. No. 17/522,553, filed Nov. 9, 2021, Wang et al.
German Office Action from counterpart DE1020231209949, dated Nov. 21, 2024.

* cited by examiner

300

310    314    318

342

342

330-1    330-2    342    330-C    341

...

...

340-1    340-2    340-C 354-1    359    358-1    374

350-1

378

370

350-2    354-2    358-2

354-C    358-C

350-C 380    388

382    384    390

BATTERY MONITORING SYSTEM FOR MEASURING HYDROGEN CONCENTRATION TO DETECT BATTERY CELL OVERTEMPERATURE AND PREDICT THERMAL RUNAWAY

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates to battery cells, and more particularly to a battery monitoring system for monitoring temperatures of battery cells.

Electric vehicles (EVs) such as battery electric vehicles (BEVs), hybrid vehicles, and/or fuel cell vehicles include one or more electric machines and a battery system including one or more battery modules each including multiple battery cells. A power control system is used to control charging and/or discharging of the battery system during charging and/or driving. A battery monitoring system monitors various parameters of the battery system and controls operation of the battery system based thereon.

SUMMARY

A battery monitoring system includes a hydrogen sensing system configured to selectively measure a plurality of hydrogen concentrations in a plurality of battery cells, respectively. A controller is configured to detect battery cell overtemperature in at least one of the plurality of battery cells in response to a corresponding one of the plurality of measured hydrogen concentrations of the plurality of battery cells.

In other features, the controller is configured to cause the hydrogen sensing system to measure a first hydrogen concentration of one of the plurality of battery cells; if hydrogen is detected, calculate a rate of increase of the hydrogen concentration; if the rate of increase of the hydrogen concentration is greater than a predetermined rate, diagnose a thermal runaway event for a corresponding one of the plurality of battery cells; and if the rate of increase of the hydrogen concentration is less than a predetermined rate, diagnose an overtemperature event for a corresponding one of the plurality of battery cells.

In other features, the controller is configured to, if the rate of increase of the hydrogen concentration is less than a predetermined rate, compare the measured hydrogen concentration to a predetermined hydrogen concentration. If the measured hydrogen concentration is greater than the predetermined hydrogen concentration, the controller is configured to diagnose overtemperature in a corresponding one of the plurality of battery cells.

In other features, the controller is configured to alter at least one of charging or discharging parameters of the plurality of battery cells in response to detecting the overtemperature. The controller is configured to cause the hydrogen sensing system to measure a first hydrogen concentration of one of the plurality of battery cells; if hydrogen is detected in the one of the plurality of battery cells, compare the measured hydrogen concentration to a predetermined hydrogen concentration; if the measured hydrogen concentration is not greater than the predetermined hydrogen concentration, increase a monitoring frequency; and if the measured hydrogen concentration is greater than the predetermined hydrogen concentration, diagnose overtemperature in a corresponding one of the plurality of battery cells.

In other features, the controller is configured to alter at least one of charging or discharging parameters of the plurality of battery cells in response to detecting the overtemperature. The hydrogen sensing system includes hydrogen sensors arranged in each of the plurality of battery cells. The hydrogen sensing system includes a hydrogen sensor that is multiplexed to sense the plurality of battery cells.

In other features, the hydrogen sensing system includes a plurality of valves, a first plurality of gas lines fluidly connecting the plurality of battery cells to inlets of the plurality of valves, and a second plurality of gas lines fluidly connected outlets of the plurality of valves.

In other feature, the hydrogen sensing system further includes a hydrogen sensor selectively connected by the plurality of valves, the first plurality of gas lines, and the second plurality of gas lines to one of the plurality of battery cells.

A method for monitoring overtemperature in a battery module including a plurality of battery cells includes selectively measuring plurality of hydrogen concentrations within a plurality of battery cells, respectively; and detecting battery cell overtemperature in at least one of the plurality of battery cells in response to a corresponding one of the plurality of the measured hydrogen concentrations of the plurality of battery cells.

In other features, the method includes measuring a first hydrogen concentration of one of the plurality of battery cells; if hydrogen is detected, calculating a rate of increase of the hydrogen concentration; if the rate of increase of the hydrogen concentration is greater than a predetermined rate, diagnosing a thermal runaway event for a corresponding one of the plurality of battery cells; and if the rate of increase of the hydrogen concentration is less than a predetermined rate, diagnosing an overtemperature event for a corresponding one of the plurality of battery cells.

In other features, if the rate of increase of the hydrogen concentration is less than a predetermined rate, comparing the measured hydrogen concentration to a predetermined hydrogen. If the measured hydrogen concentration is greater than the predetermined hydrogen concentration, diagnosing overtemperature in a corresponding one of the plurality of battery cells.

In other features, the method includes altering at least one of charging or discharging parameters of the plurality of battery cells in response to detecting the overtemperature. The method includes causing the hydrogen sensing system to measure a first hydrogen concentration of one of the plurality of battery cells; if hydrogen is detected in the one of the plurality of battery cells, comparing the measured hydrogen concentration to a predetermined hydrogen concentration; and if the measured hydrogen concentration is not greater than the predetermined hydrogen concentration, increasing a monitoring frequency; and if the measured hydrogen concentration is greater than the predetermined hydrogen concentration, diagnosing overtemperature in a corresponding one of the plurality of battery cells.

In other features, the method includes altering at least one of charging or discharging parameters of the plurality of battery cells in response to detecting the overtemperature. The method includes arranging hydrogen sensors in each of the plurality of battery cells. The method include multiplexing a hydrogen sensor to sense the plurality of battery cells.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Figures 1, 2:
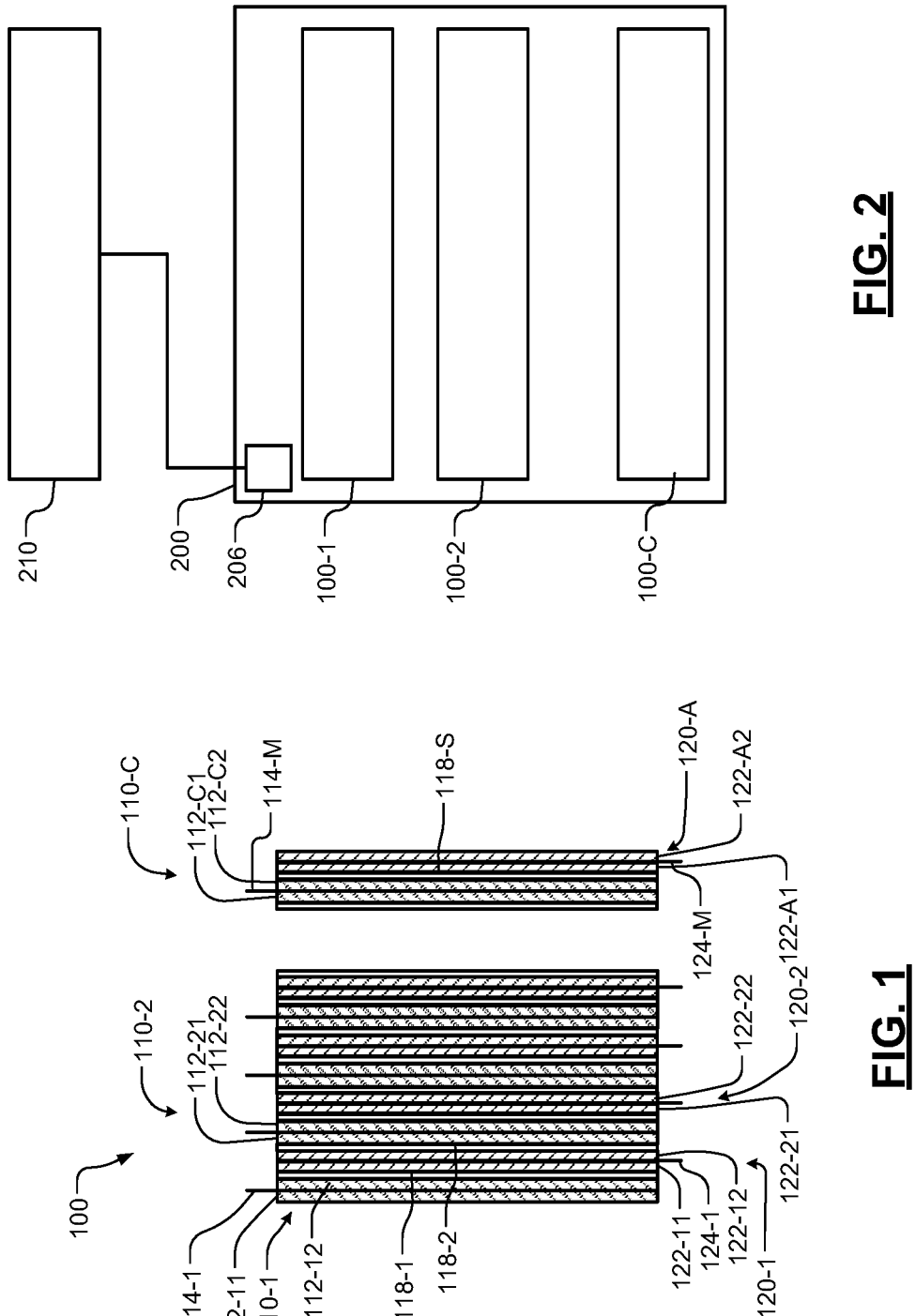
FIG. 1 is a side cross sectional view of an example of a battery cell.
FIG. 2 is a functional block diagram of an example of a battery module including a plurality of battery cells and a temperature sensor.

While the battery monitoring system is described herein in the context of EVs, the battery monitoring system can be used to monitor battery systems in stationary applications and/or in other applications.

The battery monitoring system according to the present disclosure detects overtemperature within battery cells of a battery system by monitoring hydrogen concentrations within each battery cell. In some examples, the battery cells comprise lithium-ion battery cells. Hydrogen concentrations and rates of rise can be used to predict and detect thermal runaway or other overtemperature events in the battery cells that would otherwise go undetected in other battery monitoring systems.

As described above, a battery system may include one or more battery modules each including multiple battery cells. Often, a single temperature sensor is used to monitor the temperature of the battery module but not the individual battery cells. Therefore, one of the battery cells may experience overtemperature without being detected by the temperature sensor for the battery module. The battery cell may experience thermal runaway and/or cause heating of adjacent battery cells before the temperature sensor detects a change. By the time the overtemperature is detected in these systems, it may be too late to prevent thermal runaway or other damage.

The battery monitoring system according to the present disclosure monitors molecular hydrogen ($H_2$) gas that is generated within a lithium-ion battery cell when the temperature is higher than a temperature threshold (e.g., ~70° C.). Operating temperatures of the battery cells are typically in a range from 0° C. to 55° C. during operation (and preferably 0° C. to 35° C.).

Higher than normal battery cell temperatures may occur due to thermal runaway conditions or during otherwise normal operation due to temperature gradients within the battery cells (i.e., heating near tabs, locally high resistance, and/or thermal control strategies). The battery monitoring system according to the present disclosure monitors the molecular hydrogen gas concentration and rate of rise in the enclosures of the battery cells to determine when the battery cells are operating above the temperature threshold. As a result, the battery monitoring system is able to predict and detect thermal runaway or other cell or thermal control system malfunctions so that corrective action can be taken to attempt to prevent these types of events.

The battery monitoring system samples gas from within each battery cell, continuously and/or intermittently. If the concentration of $H_2$ is above a predetermined threshold, it is likely that that the battery cell has been exposed to temperatures above a temperature threshold (e.g., ~70° C.). If monitoring continuously, the rate of increase and concentration of $H_2$ can be used to predict thermal runaway or other excessive cell overtemperature. If monitoring intermittently, the concentration can be used to detect a history of excessive cell temperature.

Referring now to FIG. 1, a battery cell 100 includes cathode electrodes 110-1, 110-2, . . . , and 110-C (collectively or individually cathode electrodes 110) and anode electrodes 120-1, 120-2, . . . , and 120-A (collectively or individually anode electrodes 120). In some examples, the cathode electrodes 110 and anode electrodes 120 are arranged in an alternating arrangement with separators 118-1, . . . , and 118-S (collectively or individually separators 118) arranged therebetween.

The cathode electrodes 110-1, 110-2, . . . , and 110-C include cathode active material 112-11, 112-12, . . . , 112-C1, and 112-C2 arranged on opposite sides of cathode current collectors 114-1, . . . , and 114-C, respectively. In some examples, the cathode current collectors are made of aluminum. The anode electrodes 120-1, 120-2, . . . , and 120-C include anode active material 122-11, 122-12, . . . , 122-C1, and 122-C2 arranged on opposite sides of anode current collectors 124-1, . . . , and 124-C, respectively. In some examples, the anode current collectors 124 are made of copper. In FIGS. 1, A, C and S are integers that are greater than one. In some examples, the battery cells include lithium-ion battery cells, and the cathode active material includes metal oxide cathode active material.

Referring now to FIG. 2, a battery module 200 includes a plurality of battery cells 100-1, 100-2, . . . , and 100-C (where C is an integer greater than one) that are arranged in an enclosure of the battery module 200. A temperature sensor 206 senses a temperature of all of the battery cells 100-1, 100-2, . . . , and 100-C in the battery module 200. The battery cells are connected in series and/or parallel arrangements.

A controller 210 is configured to monitor the temperature of the battery module 200 but not the individual battery cells. Therefore, one of the battery cells 100-1, 100-2, . . . , and 100-C may experience overtemperature without being detected by the temperature sensor 206 for the battery module 200.

A battery monitoring system according to the present disclosure samples gas from within each battery cell. If the concentration of $H_2$ is above a predetermined threshold, it is likely that that the battery cell has been exposed to temperatures above a temperature threshold (e.g., ~70° C.). If monitoring continuously, the rate of rise and concentration of $H_2$ can be used to predict thermal runaway or other excessive cell overtemperature. If monitoring intermittently, the concentration can be used to detect a history of excessive cell temperature.

Figures 3A, 3B, 3C:
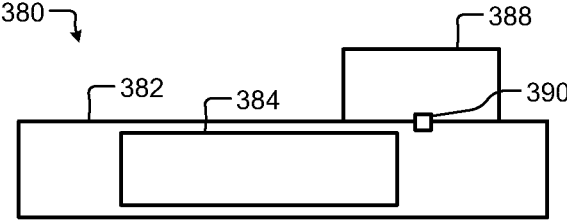
FIGS. 3A to 3C illustrate examples of battery monitoring systems including hydrogen sensing systems according to the present disclosure.

There are a variety of ways to sample concentrations of $H_2$ in the battery cells. Referring now to FIG. 3A, a plurality of battery cells 340-1, 340-2, . . . , and 340-C are selectively fluidly connected by gas lines 342 and valves 330-1, 330-2, . . . , and 330-C to a hydrogen sensor 310 and a pressure sensor 314. In other words, the hydrogen sensor 310 is multiplexed (sequentially connected by the corresponding valve and gas lines to the selected battery cell).

A vacuum pump 318 creates vacuum in the gas lines 342 to cause gases in the enclosures of the battery cells to be sampled. When sensing $H_2$, one of the valves 330 corresponding to the battery cell 340 to be sampled is opened, gas within the battery cell 340 is sampled, and $H_2$ concentrations are sensed. A controller 341 controls the valves 330, the vacuum pump 318, the hydrogen sensor 310, and the pressure sensor 314 to sample the $H_2$ concentrations in each of the battery cells 340. The controller 341 may also control charging and/or discharging of the battery cells or communicate with another controller that controls charging and/or discharging of the battery cells.

Referring now to FIG. 3B, a plurality of battery cells 350-1, 350-2, . . . , and 350-C include an electrode stack 354-1, 354-2, . . . , and 354-C, and hydrogen sensors 358-1, 358-2, . . . , and 358-C arranged in enclosures 359 of the battery cells. A controller 370 receives $H_2$ concentrations from the battery cells 350-1, 350-2, . . . , and 350-C in a wired or wireless manner. If wireless communication is used, the plurality of battery cells 350-1, 350-2, . . . , and 350-C include wireless transmitters 374 and the controller 370 communicates with a receiver 378.

Referring now to FIG. 3C, a battery cell 380 includes an electrode stack 384 arranged in an enclosure 382. In some examples, the enclosure 382 includes a pouch cell, a prismatic cell, or other type of battery cell format. A hydrogen sensor 388 is attached to the enclosure 382 and samples gas within the battery cell 380 through an opening 390 in the enclosure 382.

Figures 4, 5:
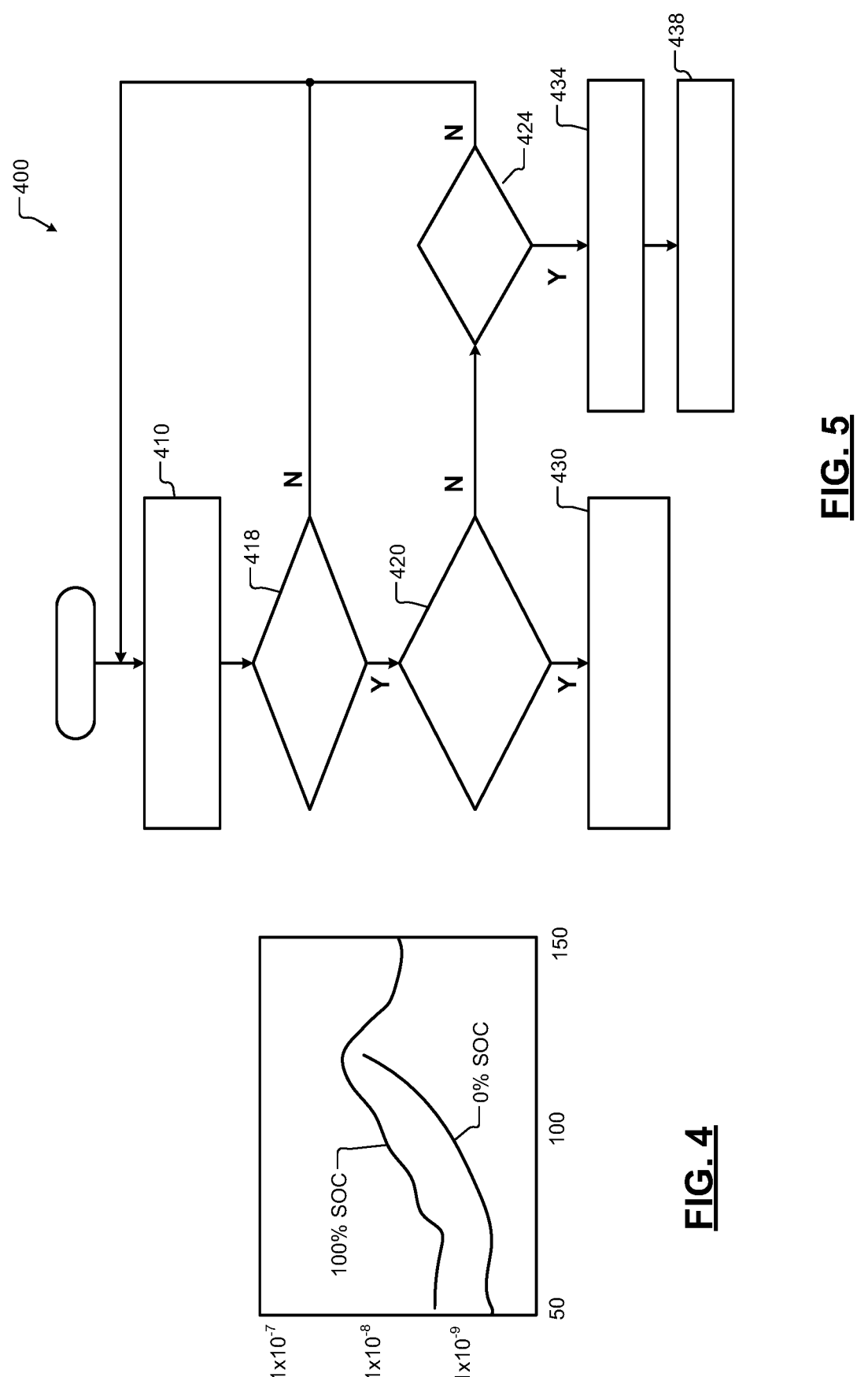
FIG. 4 is a graph illustrating measured hydrogen concentrations as a function of battery cell temperature.
FIG. 5 is a flowchart of an example of a method for monitoring a battery system to detect battery cell overtemperature based on measured hydrogen concentrations and a rate of increase of the hydrogen concentrations in each battery cell according to the present disclosure.

Referring now to FIG. 4, the concentration of $H_2$ in battery cell enclosure can be used to detect temperature increases in the battery cell. In FIG. 4, measured $H_2$ concentrations increase as a function of temperature.

Referring now to FIG. 5, a method 400 measures $H_2$ to identify overtemperature faults in the battery cells. At 410, $H_2$ concentration is monitored in each battery cell. At 418, the method determines whether $H_2$ is detected. If $H_2$ is not detected, the method returns to 410. If $H_2$ is detected, the method continues at 420. At 420, the method determines whether a rate of increase of $H_2$ is greater than a predetermined threshold. If 420 is false, the method determines whether the $H_2$ concentration is greater than a predetermined threshold at 424. If 424 is false, the method continues at 410. If 420 is true, the method reports the temperature rise and the potential for thermal runaway at 430.

If 424 is true, the method reports excess cell temperature at 434 and optionally takes remedial action at 438. For example, the controller is configured to alter a charging or discharging parameter of the battery cells in response to detecting the overtemperature. For example, a lower charging voltage, a lower charging current, a lower charging rate, a lower target SOC, etc. can be used. For example, a lower discharging voltage, a lower discharging current, a lower discharging rate, etc. can be used.

Figure 6:
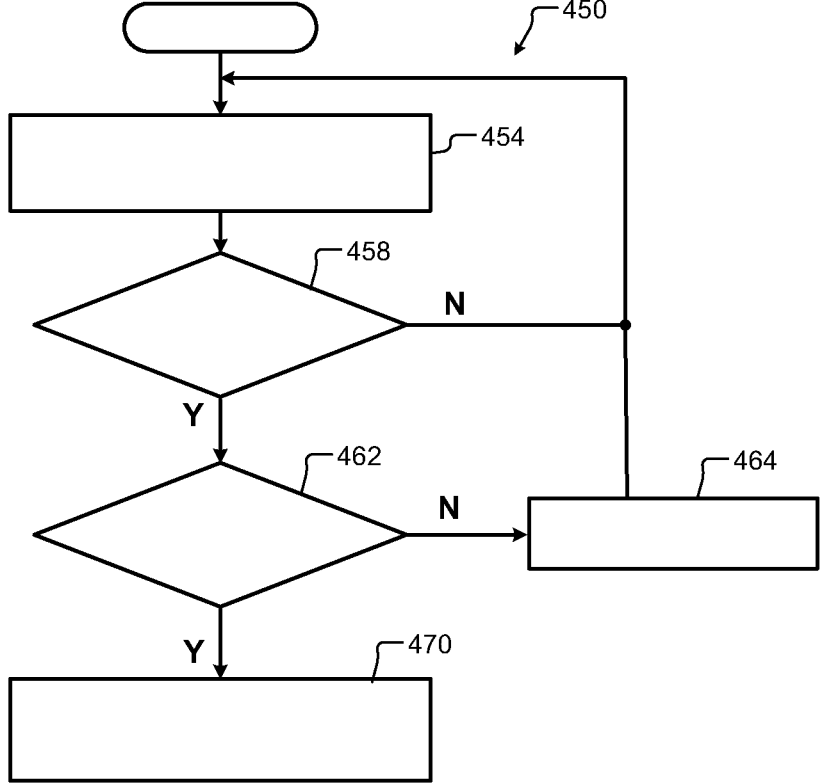
FIG. 6 is a flowchart of an example of a method for monitoring a battery system to detect battery cell overtemperature based on measured hydrogen concentrations in each battery cell according to the present disclosure.

Referring now to FIG. 6, a method 450 measures molecular hydrogen to identify overtemperature faults. At 454, the $H_2$ concentration is measured in each cell. At 458, the method determines if $H_2$ is detected. If 458 is false, the method returns to 454.

If 458 is true, the method determines whether the $H_2$ concentration is greater than a predetermined $H_2$ threshold at 462. If 462 is false, the method continues at 464 and increases the $H_2$ monitoring frequency (or reduces the predetermined sampling period between monitoring loops). If 462 is true, the method reports the temperature rise and optionally takes remedial action at 470.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information, but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A battery monitoring system comprising:
a hydrogen sensing system configured to selectively measure a plurality of hydrogen concentrations in a plurality of battery cells, respectively; and
a controller configured to detect battery cell overtemperature in at least one of the plurality of battery cells in response to a corresponding one of the plurality of hydrogen concentrations of the plurality of battery cells, wherein detecting battery cell overtemperature includes:
causing the hydrogen sensing system to measure a first hydrogen concentration of one of the plurality of battery cells;
if hydrogen is detected, calculating a rate of increase of the first hydrogen concentration;
if the rate of increase of the first hydrogen concentration is greater than a predetermined rate, diagnosing a thermal runaway event for a corresponding one of the plurality of battery cells; and
if the rate of increase of the first hydrogen concentration is less than the predetermined rate, diagnosing an overtemperature event for a corresponding one of the plurality of battery cells.

2. The battery monitoring system of claim 1, wherein the controller is configured to:
if the rate of increase of the first hydrogen concentration is less than the predetermined rate, compare the first hydrogen concentration to a predetermined hydrogen concentration; and
if the first hydrogen concentration is greater than the predetermined hydrogen concentration, diagnose the overtemperature event in a corresponding one of the plurality of battery cells.

3. The battery monitoring system of claim 1, wherein the controller is configured to alter at least one of charging or discharging parameters of the plurality of battery cells in response to detecting the overtemperature event.

4. The battery monitoring system of claim 1, wherein the controller is configured to:
if hydrogen is detected in the one of the plurality of battery cells, compare the first hydrogen concentration to a predetermined hydrogen concentration;
if the first hydrogen concentration is not greater than the predetermined hydrogen concentration, increase a monitoring frequency; and if the first hydrogen concentration is greater than the predetermined hydrogen concentration, diagnose the overtemperature event in a corresponding one of the plurality of battery cells.

5. The battery monitoring system of claim 4, wherein the controller is configured to alter at least one of charging or discharging parameters of the plurality of battery cells in response to detecting the overtemperature event.

6. The battery monitoring system of claim 1, wherein the hydrogen sensing system includes hydrogen sensors arranged in each of the plurality of battery cells.

7. The battery monitoring system of claim 1, wherein the hydrogen sensing system includes a hydrogen sensor that is multiplexed to sense the plurality of battery cells.

8. The battery monitoring system of claim 7, wherein the hydrogen sensing system includes:
a plurality of valves;
a first plurality of gas lines fluidly connecting the plurality of battery cells to inlets of the plurality of valves; and
a second plurality of gas lines fluidly connected to outlets of the plurality of valves.

9. The battery monitoring system of claim 8, wherein the hydrogen sensing system further includes a hydrogen sensor selectively connected by the plurality of valves, the first plurality of gas lines, and the second plurality of gas lines to one of the plurality of battery cells.

10. A method for monitoring overtemperature in a battery module including a plurality of battery cells, comprising:
selectively measuring a plurality of hydrogen concentrations within a plurality of battery cells, respectively; and
detecting battery cell overtemperature in at least one of the plurality of battery cells in response to a corresponding one of the plurality of the hydrogen concentrations of the plurality of battery cells, wherein detecting battery cell overtemperature includes:
measuring a first hydrogen concentration of one of the plurality of battery cells;
in response to detecting hydrogen in the one of the plurality of battery cells, comparing the first hydrogen concentration to a predetermined hydrogen concentration;

in response to the first hydrogen concentration being less than or equal to the predetermined hydrogen concentration, increasing a monitoring frequency; and
in response to the first hydrogen concentration being greater than the predetermined hydrogen concentration, diagnosing an overtemperature event in a corresponding one of the plurality of battery cells.

11. The method of claim 10, further comprising:
if hydrogen is detected, calculating a rate of increase of the first hydrogen concentration;
if the rate of increase of the first hydrogen concentration is greater than a predetermined rate, diagnosing a thermal runaway event for a corresponding one of the plurality of battery cells; and
if the rate of increase of the first hydrogen concentration is less than the predetermined rate, diagnosing the overtemperature event for a corresponding one of the plurality of battery cells.

12. The method of claim 11, wherein:
if the rate of increase of the first hydrogen concentration is less than the predetermined rate, comparing the first hydrogen concentration to the predetermined hydrogen concentration; and
if the first hydrogen concentration is greater than the predetermined hydrogen concentration, diagnosing the overtemperature event in a corresponding one of the plurality of battery cells.

13. The method of claim 10, further comprising altering at least one of charging or discharging parameters of the plurality of battery cells in response to detecting the overtemperature event.

14. The method of claim 12, further comprising altering at least one of charging or discharging parameters of the plurality of battery cells in response to detecting the overtemperature event.

15. The method of claim 10, further comprising arranging hydrogen sensors in each of the plurality of battery cells.

16. The method of claim 10, further comprising multiplexing a hydrogen sensor to sense the plurality of battery cells.

* * * * *